(12) United States Patent
Carver et al.

(10) Patent No.: US 9,155,474 B2
(45) Date of Patent: Oct. 13, 2015

(54) SYSTEM FOR MULTISPECTRAL IMAGING OF FLUORESCENCE

(71) Applicants: Gary E. Carver, Wilmington, VT (US); Sheetal K. Chanda, Brattleboro, VT (US); William A. Morrison, East Dummerston, VT (US); Sarah A. Locknar, South Pomfret, VT (US); Robert L. Johnson, Jr., Brattleboro, VT (US)

(72) Inventors: Gary E. Carver, Wilmington, VT (US); Sheetal K. Chanda, Brattleboro, VT (US); William A. Morrison, East Dummerston, VT (US); Sarah A. Locknar, South Pomfret, VT (US); Robert L. Johnson, Jr., Brattleboro, VT (US)

(73) Assignee: Omega Optical, Inc., Brattleboro, VT (US)

( * ) Notice: Subject to any disclaimer, the term of this patent is extended or adjusted under 35 U.S.C. 154(b) by 93 days.

(21) Appl. No.: 13/966,639

(22) Filed: Aug. 14, 2013

(65) Prior Publication Data

US 2015/0051497 A1    Feb. 19, 2015

(51) Int. Cl.
| | |
|---|---|
| *A61B 5/00* | (2006.01) |
| *A61N 5/06* | (2006.01) |
| *A61B 1/00* | (2006.01) |
| *A61B 1/04* | (2006.01) |
| *A61B 1/07* | (2006.01) |
| *A61B 18/20* | (2006.01) |

(52) U.S. Cl.
CPC ............... *A61B 5/0071* (2013.01); *A61B 1/00* (2013.01); *A61B 1/043* (2013.01); *A61B 1/07* (2013.01); *A61B 5/0059* (2013.01); *A61B 5/0068* (2013.01); *A61B 5/0075* (2013.01); *A61B 18/20* (2013.01); *A61N 5/062* (2013.01)

(58) Field of Classification Search
None
See application file for complete search history.

(56) References Cited

U.S. PATENT DOCUMENTS

| | | | | |
|---|---|---|---|---|
| 5,037,180 | A | 8/1991 | Stone | |
| 5,953,477 | A * | 9/1999 | Wach et al. | ............... 385/115 |
| 6,429,968 | B1 | 8/2002 | Carver | |
| 6,452,681 | B1 | 9/2002 | Carver et al. | |
| 7,366,365 | B2 | 4/2008 | Carver | |
| 7,702,381 | B2 * | 4/2010 | Gaeta et al. | ............... 600/478 |
| 7,817,267 | B2 | 10/2010 | Carver | |
| 2008/0097225 | A1 * | 4/2008 | Tearney et al. | ............... 600/478 |

(Continued)

OTHER PUBLICATIONS

Multimode vs. Singlemode—Fiber Fundamentals (Meridian Technologies, http://www.meridian-tech.com/support/articles, Nov. 2008).*

(Continued)

*Primary Examiner* — Unsu Jung
*Assistant Examiner* — Carolyn Pehlke
(74) *Attorney, Agent, or Firm* — John de la Rosa

(57) ABSTRACT

A confocal scanning system for the multispectral imaging of fluorescence from a tissue sample based on time domain mapping of spectral components of the fluorescence using coated fiber tips disposed on multimode optical fibers. A fiber grating spectrometer based on two serial arrays of coated fiber tips disposed on multi-mode fiber, and delay lines between them provide spectral slices of the florescence. The coated fiber tips are arranged such that the shortest wavelength spectral components are reflected first and the longest wavelength components last. Fiber-based delay lines delay the reflections from each successive fiber tip such that they are uniformly separated in time, and in the order of its spectral wavelength number. The spectral bins are used to colorize the images to show the presence of abnormal tissue at cellular spatial resolution. A second scan with increased laser flux can destroy the diseased tissue revealed by the first scan.

19 Claims, 9 Drawing Sheets

(56) References Cited

U.S. PATENT DOCUMENTS

2010/0020319 A1* 1/2010 Demos et al. ............... 356/301
2010/0234684 A1* 9/2010 Blume et al. ............... 600/104

OTHER PUBLICATIONS

Donnelly, Judith and Massa, Nicholas (Light—Introduction to Optics and Photonics, Chapter 11: Introduction to Fiber Optics, Jan. 2010).*

Bahaa E. A. Saleh, Malvin Carl Teich, Fundamentals of Photonics, Chapter 3: Beam Optics (1991).*

Ramasamy, Ranjith, et al. "Multiphoton imaging and laser ablation of rodent spermatic cord nerves: potential treatment for patients with chronic orchialgia." The Journal of urology 187.2 (2012): 733-738.*

Optics of Gaussian Beams (http://www.ece.umd.edu/~davis/chapter16.pdf, Jun. 11, 2010).*

Helmchen, Fritjof, David W. Tank, and Winfried Denk. "Enhanced two-photon excitation through optical fiber by single-mode propagation in a large core." Applied optics 41.15 (2002): 2930-2934.*

SM Fiber for Visible RGB Through to Near IR (Fibercore, http://fibercore.com/product/sm-fiber-for-visible-rgb-through-to-near-ir, 2015.

Cut-off wavelength (Fibercore, http://fibercore.com/expertise/fiberpaedia/cut-off-wavelength, 2015).

Photonics Technical Note #21 Fiber Optics (Newport Corporation, http://assets.newport.com/webDocuments-EN/images/Fiber-Basics.pdf, 2015).

* cited by examiner

SYSTEM FOR MULTISPECTRAL IMAGING OF FLUORESCENCE

This invention was made with government support under SBIR Phase II Grant Number 5R44CA124036-03 awarded by National Cancer Institute through the National Institutes of Health.

RELATED APPLICATION

This application claims the benefits of U.S. Provisional Application No. 61/760,308 filed Feb. 4, 2013, entitled "System and Method for Multispectral Imaging of Intrinsic Fluorescence," which application is incorporated herein by reference in its entirety.

BACKGROUND OF THE INVENTION

Various imaging systems and techniques have been used for biomedical applications, such as tissue mapping. One approach to tissue mapping involves multispectral imaging, where the tissue to be mapped is conjugate with a detector array, such as charge coupled device (CCD) or a photo-diode array. In the array, the spatial data is directly obtained in the image. A tunable filter, such a liquid crystal filter (LCTF) or acousto-optical tunable filter (AOTF) can be placed before the detector array, and images collected for each color setting of the filter. Alternatively, a volume hologram can be placed before the detector array, with images collected by pixel arrays positioned where each color is diffracted.

The above imaging systems, however, are generally limited in terms of temporal response time, typically about 25 microseconds (for the AOTF) to 100 milliseconds (for the LCTF) per wavelength. For weak intrinsic fluorescence, these later systems also have long array integration times, leading to multispectral-image acquisition times of several seconds—which are too long for live biological samples. Other approaches use confocal microscopy where high resolution images are obtained using a condenser lens to focus illuminating light from a point source into a diffracted limited spot within a specimen. An objective lens then focuses the light emitted from that spot onto a small pinhole and a detector measures the amount of light passing through the pinhole. Because only light from within the illuminated spot is focused through the pinhole, any stray light is filtered out, greatly improving the image quality. A coherent image is created by scanning point by point over the desired field of view, and recording the intensity of the light emitted from each spot, as small spots are illuminated at any one time. Scanning can be accomplished in several ways, such as laser scanning.

Multi-spectral confocal mapping holds great promise for imaging cancer cells at the cellular and molecular levels. Indeed, the National Institute of Health (NIH) has encouraged research and development pertaining to in-vivo image guided cancer interventions. Also, many cancers can be detected with multi-spectral imaging of fluorescence. See Thiberville, L., Moreno-Swirc, S., Vercauteren, T., Peltier, E., Cave, C., Heckly, G. B., "In Vivo Imaging of The Bronchial Wall Microstructure Using Fibered Confocal Fluorescence Microscopy," Am J Respir Crit Care Med 175, 22-31 (2007); Fu, S., Chia, T. C., Kwek, L. C., Diong, C. H., Tang, C. L., Choen, F. S., Krishnan, S. M., "Application of Laser Induced Autofluorescence Spectra Detection In Human Colorectal Cancer Screening," Proc. SPIE-OSA Biomedical Optics 5141, 298-304 (2003); and Ramanujan, V. K., Ren, S., Park, S., Farkas, D. L., "Non-Invasive, Contrast-Enhanced Spectral Imaging of Breast Cancer Signatures In Preclinical Animal Models In Vivo," J Cel Sci Therapy 1, 102-106 (2010).

Moreover, spectroscopic tools can provide multi-spectral data during laser excitation of fluorescence, 2-photon, and Raman spectroscopies, especially useful where samples are labeled with a variety of molecular-specific contrast agents. Multi-spectral imaging is typically done with one grating and multiple pixels in a detector array, but this approach is limited by read-out noise and dark current. As such, most biomedical applications center on labeled tissue and/or the use of costly PMT arrays, preventing clinical applications in humans. This latter limitation is addressed in U.S. Pat. No. 7,366,365 entitled "Tissue Scanning Apparatus and Method." In this latter patent, there is described a system for multispectral confocal mapping of tissue suitable for scanning in-vivo or ex-vivo tissues where spectra can be acquired for each pixel in a confocal spatial scan. More particularly, there is described a confocal spatial scan system in conjunction with a fast fiber Bragg grating spectrometer. This combination maps wavelengths into time slots and is fiber based. The fiber that connects the fast optical spectrum analyzer to the scanner functions as the pinhole in a confocal microscope. That is, the cleaved end of fiber provides the confocal pinhole. The spectrum analyzer provides spectra derived from un-blazed fiber Bragg gratings that have delay lines between the gratings. The use of a single detector in a confocal arrangement easily offers spectral resolutions of about 1-2 nm.

Unfortunately, this latter approach above cannot offer spectral resolution above 10 nm in a practical and cost effective manner, a regime particularly useful for applications in humans such as optical biopsy and surgical margin assessments. Moreover, the fiber Bragg gratings in the '365 patent are realized using single mode fiber typically having a core diameter of about 3 μm, thereby limiting the collection efficiency, impractical for weak intrinsic fluorescence.

SUMMARY OF THE INVENTION

The present invention is a confocal scanning system for the multispectral imaging of intrinsic fluorescence from a tissue sample based on the mapping of the spectral components of the fluorescence into the time domain using thin film optical filters deposited on the tips of multimode optical fibers or so called "coated fiber tips."

In one embodiment, confocal scanning is effected using two scanning mirrors that scan a focused laser beam on the tissue sample with the focused spot kept conjugated with the entrance aperture of the multi-mode fiber. For endoscopy, a coherent fiber bundle with about 30,000 three micron diameter fibers is used to transfer the beam to the tissue. A fiber grating spectrometer based on two serial arrays of coated fiber tips disposed on multi-mode fiber, and delay lines between them provide spectral slices of the fluorescence. The coated fiber tips are arranged such that the shortest wavelength spectral components are reflected first and the longest wavelength components last. Fiber-based delay lines delay the reflections from each successive coated fiber tip such they are uniformly separated in time to assigned spectral bins, and in the order of its spectral wavelength number.

With a low angle injection at the confocal aperture, the angle of incidence (AOI) inside the multi-mode fiber is closer to a Gaussian than a Lambertian source such that the reflectance characteristics of the coated fiber tip remain substantially unaffected by the AOI The large core confocal aperture collects light from nearest and next nearest sub-fibers of the fiber bundle, assisting in the efficient collection of low light level intrinsic fluorescence. The spectral bins are used to colorize the tissue images to show the presence of abnormal tissue at cellular-level spatial resolution.

BRIEF DESCRIPTION OF THE DRAWINGS

The features and advantages of the present invention will become more readily apparent from the following detailed description of the invention in which like elements are labeled similarly and in which.

DETAILED DESCRIPTION

The present invention is a confocal scanning system for the multispectral imaging of intrinsic fluorescence from tissue excited, for example, with blue or violet radiation, applicable to optical biopsy, microscopy, endoscopy and cytometry. It is based, in part, on the mapping of the spectral components of the intrinsic fluorescence into the time domain using thin film coated fiber tip filters disposed on multimode optical fibers, as discussed more fully herein below.

In general, the confocal spatial scan is employed in conjunction with thin film coated fiber tip filters or so-called "coated fiber tips." See, for example, U.S. Pat. No. 5,037,180, which is incorporated herein by reference. The coated fiber tips have interference filters comprised of a multilayer thin-film stack of low and high index of refraction material that is deposited judiciously onto the end of multi-mode optical fibers. Coated fiber tips function to map spectral "slices" or bins of the intrinsic fluorescence into the time domain. Each coated fiber tip reflects wavelengths up to a transition level while transmitting longer wavelengths, and advantageously provides spectral slices greater than 10 nm—sufficient for distinguishing between diseased and healthy tissue. A serial array of such coated fiber tips allows mapping many spectral bins into the time domain with efficiency compatible with the low levels encountered in detecting intrinsic fluorescence through endoscopes. Importantly, the large core fiber that connects the coated fiber tips to the scanner functions as the confocal aperture, while allowing the fluorescence to propagate within the fiber as a Gaussian-like beam. The larger confocal aperture also captures more scattered emission than single mode fiber, although with less spectral and spatial resolution, but sufficient for distinguishing between diseased and healthy tissue.

Without any loss of generality or applicability for the principles of the invention, it is to be understood that the figures and descriptions of the present invention have been simplified to illustrate the elements that are relevant for a clear understanding of the present invention, while eliminating, for purpose of clarity, many other elements. However, because such elements are well known in the art, and because they do not facilitate a better understanding of the invention, a discussion of such elements is not provided herein. The disclosure herein is directed to all such variations and modifications known to those skilled in the art.

Figure 1:
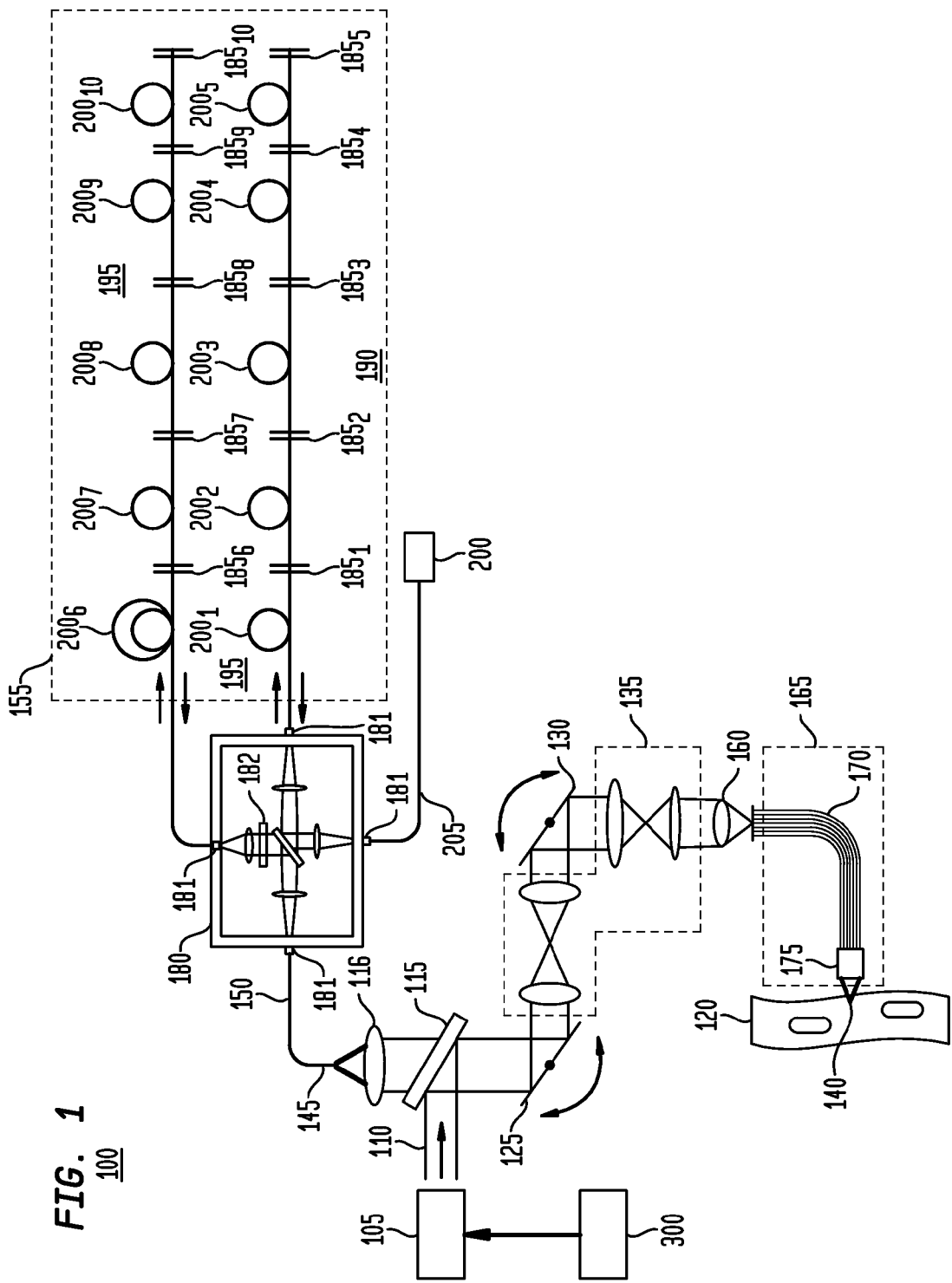
FIG. 1 is a block diagram showing a confocal multispectral imaging system in accordance with the principles of the invention.

Referring to FIG. 1 there is shown a diagram depicting a confocal multispectral imaging system 100 according to an embodiment of the invention well suited for endoscopy. System 100 is well suitable for scanning in-vivo as described herein below. System 100 broadly encompasses the concept that multispectral imaging of intrinsic fluorescence can be acquired in a confocal spatial scan using coated fiber tips.

System 100 includes a pulsed radiation source 105 providing an excitation beam 110 entering the system by reflecting from a dichroic splitter 115. The excitation is provided by, for example, a pulsed 488 nm or 405 nm laser. Averaged over 1 second, the excitation levels at tissue sample 120 are in the 1 to 2 mw range and should be limited to about 5 mw for operating room safety reasons and to avoid potential tissue damage in the subject. When excited with blue or violet radiation, intrinsic fluorescence from, for example flavins and porhyrins, within tissue sample 120 occurs in the visible wavelength range. For a discussion of the fluorescence characteristics of biological materials in the tissue or cell structure, see for example, Wagnieres, Start, Wilson, "Photochemistry and Photobiology," 68(5) 1998. A low duty cycle pulsed source allows for sufficient peak power without bleaching or tissue damage. Of course, the excitation radiation could be of any wavelength, or group or range of wavelengths useful in tissue scanning. In-vivo applications on living tissue, however, usually avoid hard UV wavelengths that can cause tissue damage. Excitation in the form of a substantially single frequency laser line, however, is useful for inducing fluorescence. Moreover, fluorescence can occur within the infrared spectrum.

Confocal scanning is shown by two scanning mirrors 125, 130 and associated optics 135. As mirrors 125, 130 scan excitation beam 110 in X-Y raster pattern on the tissue sample, associated optics 135 operates together with the mirrors in a conventional manner to keep focused spot 140 always conjugate with entrance aperture 145 of multi-mode fiber 150. Doing so limits the acceptance of light from axial and lateral locations away from the position of focused spot 140. The intrinsic fluorescence is a spectrally broad signal generated by the tissue sample based on the excitation from the pulsed radiation source. The spectrally broad light from the tissue sample is returned through scanning mirrors 125, 130. Objective lens 116 focuses the light onto fiber 150 to fiber based spectrometer 155 that maps different spectral components into the time domain.

Since fluorescence from biological tissues typically occurs within 1 to 5 ns after excitation, this fluorescence propagates back to the confocal aperture before the mirrors can move appreciably. This allows the mirrors to de-scan the back-propagating light so that the light from the focused spot is conjugate with entrance aperture 145 of fiber 150. As a result, scanning confocal system 100 can generate maps or images of the tissue sample with spatial resolution at or near the laser spot size.

System 100 performs microscopy when the tissue sample is placed at the focus of objective lens 160, and endoscopy when the proximal end of an endoscope 165 is placed in the same location. For endoscopy, a coherent fiber bundle 170 with about 30,000 three micron diameter fibers having a grin lensed distal tip 175 is placed under objective lens 160. Fiber bundle 170 can be inserted as an imaging fiber bundle into a body cavity or other aperture to perform endoscopy. Our large core confocal aperture collects light from nearest and next nearest sub-fibers—assisting in the efficient collection of low light level intrinsic fluorescence. The confocal scanner raster scans the proximal end of fiber bundle 170 where it is transferred to the distal end and grin lens 175 relays the beam from the fiber to the tissue sample. Fluorescence or reflected light from a resolution element on the tissue sample is imaged back into the same fiber bundle 170 and propagates back to the proximal end. This latter light is collected and de-scanned by mirrors 125, 130 and focused on the entrance aperture of optical fiber 150 that acts as a confocal pinhole. The entire process occurs within the dwell time of the raster scan of about 2.5 microseconds. For endoscopy, excitation beam 110 is focused by the distal grin lens 175 at NA of 0.8 (creating a 0.4 μm diameter spot) and scanned over an adjustable field at a working distance of about 80 μm.

In the preferred embodiment, fiber spectrometer 155 is based on two serial arrays of coated fiber tips disposed on multi-mode fiber, and delay lines between these elements. Thin film coated fiber tips disposed on multimode fiber increase the collection efficiency relative to single mode fiber. Coated fiber tip arrays can be fabricated on many fiber types, including 10 μm and 62.5 μm core multi-mode fibers. Each coated fiber tip is physically attached to another fiber such that the thin film coatings are immersed between glass on both sides. The 62.5 μm diameter core fiber increases collection efficiency about 7 times over the 10 μm core fiber. To minimize loss, optical contact is required between the fibers and the coated fiber tips. Of course, the thin film coatings are hard enough to tolerate FC/FC couplings. Results from experimental practice indicate that a thin film stack of micron thick YF3 and ZnS is sufficiently hard enough in an immersed coating configuration of glass/filter/glass to meet these latter mechanical constraints. Other hard or semi-hard high and low index combinations are possible, such as $TiO_2/SiO_2$; $Nb_2O_5/SiO_2$; and $HfO_2/SiO_2$.

After excitation, the fluorescence from the biological sample is coupled back through the confocal scanner through dichroic splitter 115 and coupled through optics 180 to a serial array of multiple coated fiber tips $185_1$, $185_2$, $185_3$, ... $185_{10}$ distributed between two multi-mode optical fiber legs, 190 (blue leg) and 195 (red leg). Coupling optics 180 operates in a conventional manner and also redirects the reflected light from the coated fiber tips to a high gain, low noise detector 200, such as a photomultiplier tube (PMT) or single photon array. As shown, coupling optics 180 have been fitted with optical FC connectors 181 to facilitate connection to fiber spectrometer 155. Coated fiber tips $185_1$, $185_2$, $185_3$ ... $185_{10}$, have reflectance matching wavelengths designated as $\lambda_1$, $\lambda_2$, $\lambda_3$ ... $\lambda_{10}$, respectively. Coupling optics 180 may include discrete optics (shown), fiber pig-tailed splitters, or optical circulators.

As discussed herein below, a 5 spectral bin design per leg propagates 30% of the light incident on the array back out of the coated fiber tip array. This factor drops to 7% for 10 bins per leg. The thin film coated fiber tips may be configured to maximize throughput by placing 5 bins on each leg of a fiber pigtailed splitter. Of course, the goal is to use enough spectral bins to colorize an image that clearly shows the presence of abnormal tissue at cellular spatial resolution. Additionally, optical circulators which are becoming available in the visible spectrum can also be used. For an application requiring only up to 5 bins, a fiber pigtailed splitter can be populated with two identical legs. This effectively avoids half of the loss caused by the splitter. The extra delay is still added to the second leg to avoid interference.

Figure 2:
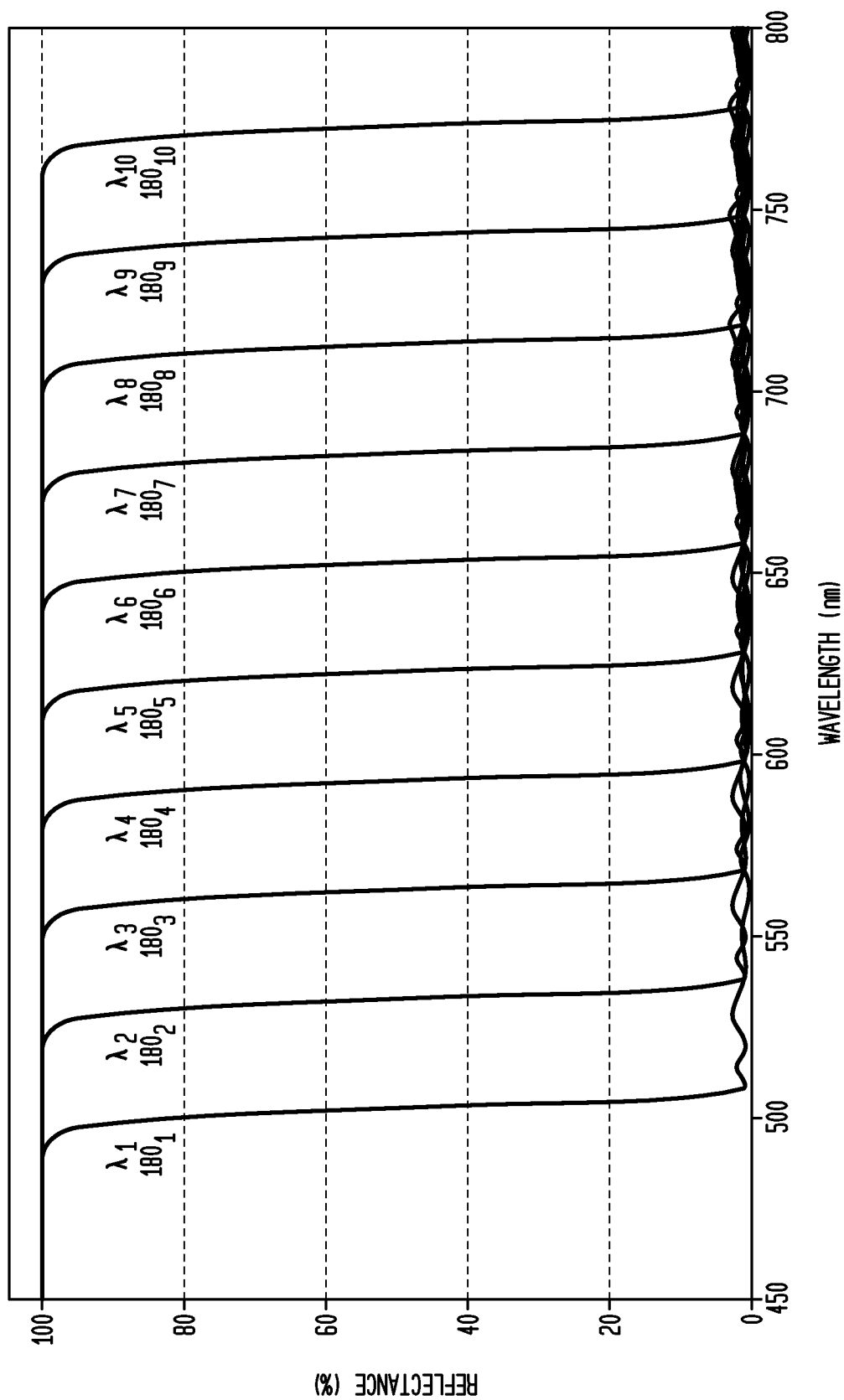
FIG. 2 is a graph illustrating the reflectance of coated fiber tip filters to effect "spectral slicing;"

While only five (5) coated fiber tips and fiber delay loops are shown in each optical fiber leg, each may consist of numerous such coated fiber tips and delay loops. Each coated fiber tip enables wavelength selection at its corresponding matching wavelength by reflecting up to a transition wavelength while transmitting longer wavelengths thereby providing spectral slices of the fluorescence. Referring to FIG. 2, there is shown exemplary reflectance of the coated fiber tips spaced 30 nm apart to effect a so-called "spectral slicing" function. Importantly, note that the reflectance band for each coated fiber tip is offset to uniquely match the desired "sliced" spectral components or spectral bin of the fluorescence. Optical path delays $200_1$, $200_2$, $200_3$ ... $200_{10}$ are provided between coated fiber tips $185_1$ ... $185_{10}$, respectively. Each delay may take the form of a length or loop of optical fiber that introduces a time delay as the light propagates forward and back.

Fluorescence of wavelength $\lambda_1$ is reflected by coated fiber tip $185_1$. Light of wavelength $\lambda_2$ is reflected by coated fiber tip $185_2$. Light of $\lambda_3$ is reflected by coated fiber tip $185_3$ and so on until wavelength of $\lambda_{10}$ is reflected by coated fiber tip $185_{10}$. Light of wavelength $\lambda_1$ is first to arrive at optical detector 200 as it enters coupling optics 180 and is directed through multi-mode optical fiber 205 into detector 200. The reminder of the light reflected by fiber tip filters $185_2$, $185_3$ ... $185_{10}$ is delayed by delay lengths or loops $200_2$, $200_3$, ... $200_m$, respectively, such that the next light that arrives at the detector is of wavelength $\lambda_2$, and so on. That is, the coated fiber tips are arranged such that the shortest wavelength spectral components are reflected first and the longest wavelength components last. That is, fiber-based delay lines ($200_1$ ... $200_{10}$), judiciously disposed between each coated fiber tip, delay the reflections from each successive fiber tip such that each spectral component is correspondingly delayed so as to be uniformly separated in time, and in the order of its spectral wavelength number (i.e., $\lambda_1 < \lambda_2 < ... \lambda_{10}$). In doing so, each spectral component is thus allocated a unique spectral bin slot within the time domain for conversion into an electrical signal by optical detector 200. Since the amplitude peaks of the electrical signal correspond to the optical power in the spectral components of the fluorescence signal, a display of the optical power as a function of wavelength can be readily obtained. The operating principle of a wavelength slicer, however, is more fully described in U.S. Pat. No. 6,452,681, which is incorporated herein by reference.

Since all colors propagate in both optical fiber legs 190, 195—the red light simply propagates off the end of blue leg 190, but blue light will reflect from the filters in red leg 195 and pollute the red bins with blue light, contributing to crosstalk. A blue absorber 182 placed at the beginning of red fiber leg 195 can minimize the crosstalk by filtering the undesired wavelengths. Alternatively, passband coated fiber tips may be used in the red fiber leg rather than low wavelength filters.

It should be understood that the serial array of such coated fiber tips allows mapping many spectral bins (wavelengths) into the time domain with efficiency compatible with the low levels encountered in detecting intrinsic fluorescence through endoscopes. The large core fiber that connects the coated fiber tips to the scanner functions as the confocal aperture. This larger confocal aperture captures more scattered or out-offocus emission, although with less spectral and spatial resolution, but sufficient for distinguishing between diseased and healthy tissue.

Again, the fluorescence of interest typically occurs between 500-800 nm. About 10 spectral bins each 30 nm wide is sufficient to sample the visible spectra of the fluorescence for applications in optical biopsy, as shown in FIG. 2. The bluest filter is mapped into the first spectral bin ($\lambda_1$), and the reddest filter is mapped into the last spectral bin ($\lambda_{10}$). The spectral width and edges of the bins are adjustable and can be configured to minimize false positive and false negatives for specific diseases. If needed, a fiber switch (not shown) may be employed to connect disease or organ specific fiber tip arrays as needed in the clinic. A fiber tip array can easily be customized to detect a specific disease in a specific organ by adjusting the center wavelength and spectral width of each bin.

A fiber optic spectrometer based on prior art fiber Bragg gratings is impractical in detecting weak intrinsic fluorescence. Fiber Bragg gratings require single mode fibers of about 3 μm core diameter to operate in the visible spectrum. However, confocal operation with such diameter fibers would exhibit an extremely weak signal that is barely above the shot noise limit. The use of fiber Bragg gratings in larger multi-mode fibers is not a solution because the higher order modes impact the gratings over a wide angular distribution and are therefore diffracted over a distribution of wavelengths.

Figure 3:
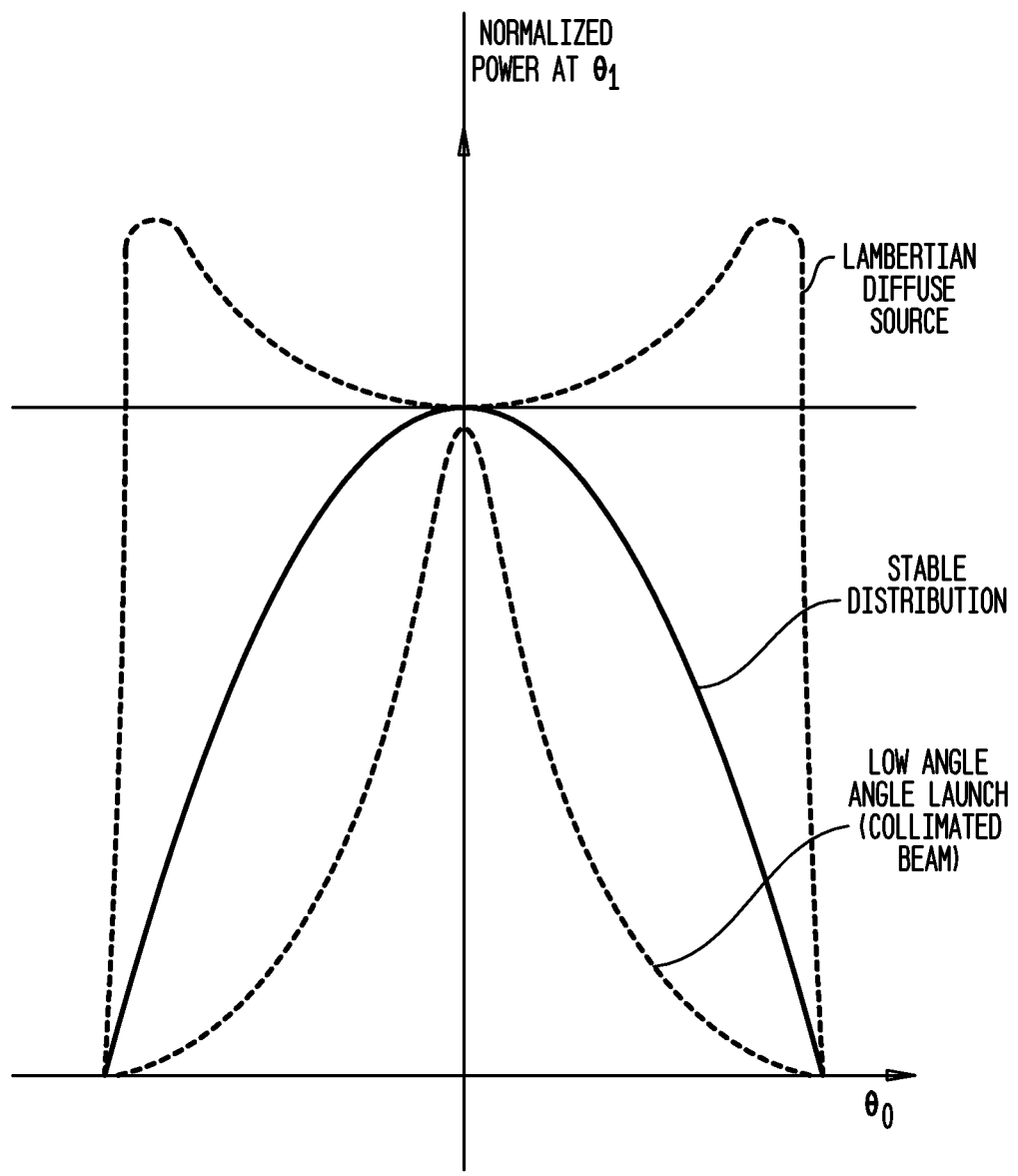
FIG. 3 is an exemplary graph of the angular power distribution of the light in multi-mode fiber.
Figure 4:
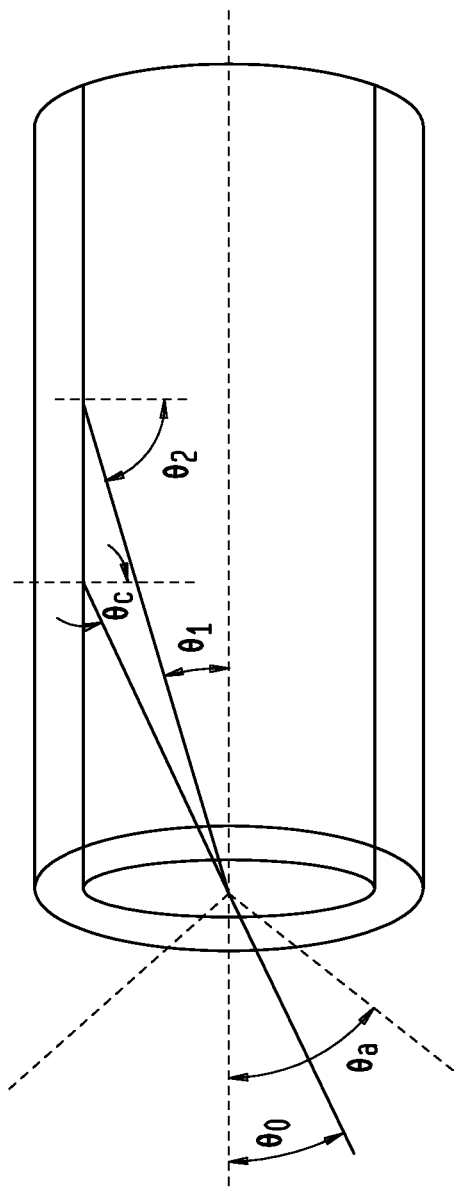
FIG. 4 depicts the relationship between the acceptance angle and the refractive indices of multi-mode fiber.

Optical analysis, however, indicates that the angular power distribution in the multimode fiber does not appreciably affect the spectral reflectance of the coated fiber tips if a low angle of injection is used, as discussed herein below. Shown in FIG. 3 is the typical angular power distribution in a multi-mode fiber. Those skilled in the art will note that the angular distribution is a function of the launch conditions, $\theta_0$. Only incident light entering the multimode fiber within an acceptance angle $\theta_a$ propagates within the fiber. The acceptance angle is related to the refractive indices of the core and cladding. FIG. 4 illustrates the relationship between the acceptance angle and the refractive indices. Assuming the entrance face at the fiber core to be normal to the axis, and applying Snell's law we have then that numerical aperture (NA):

$$NA = (n_{core}^2 - n_{clad}^2)^{1/2} \quad (1)$$

where $n_{core}$ is index of refraction of the fiber core; and $n_{clad}$ is the index of refraction of the fiber cladding.

Typical values of the NA range from 0.10 to 0.48 for glass fibers. For a Lambertian source used to populate all the modes in a fiber with a numerical aperture of, for example 0.4, the maximal acceptance angle $\theta_a$ is about 24°. The incident light at angle $\theta_0$ is refracted at angle $\theta_1$ upon entering the fiber and is then transmitted to the core-cladding interface where it then strikes the core-cladding interface at an angle $\theta_2$. The light is totally reflected back into the core and continues to propagate within the fiber in this manner. Incident light, however, that enters the fiber at an angle greater than $\theta_a$ is refracted upon entering the fiber and is transmitted to the core-cladding interface, but strikes the core-cladding interface at an angle less than the critical angle $\theta_c$. This light is refracted into the cladding and is eventually lost. As such, light incident on the fiber core must be within the acceptance cone defined by the angle $\theta_a$ as shown in FIG. 4.

The present invention judiciously uses a low angle injection ($\theta_0$) of about 6 degrees at the confocal aperture. Due to Snell's' law, the angle of incidence $\theta_1$ at the fiber tip within the multi-mode fiber is about 4 degrees, well below the critical angle of the fiber. At these small angles, the angular power distribution inside the multi-mode fiber is closer to a Gaussian than a Lambertian source (FIG. 3). As a result, the angle of incidence (AOI) at the fiber tips is within a few degrees of normal incidence. Operation near normal incidence allows the reflectance of the fiber tips to exhibit sharp transitions as a function of wavelength.

Figure 5:
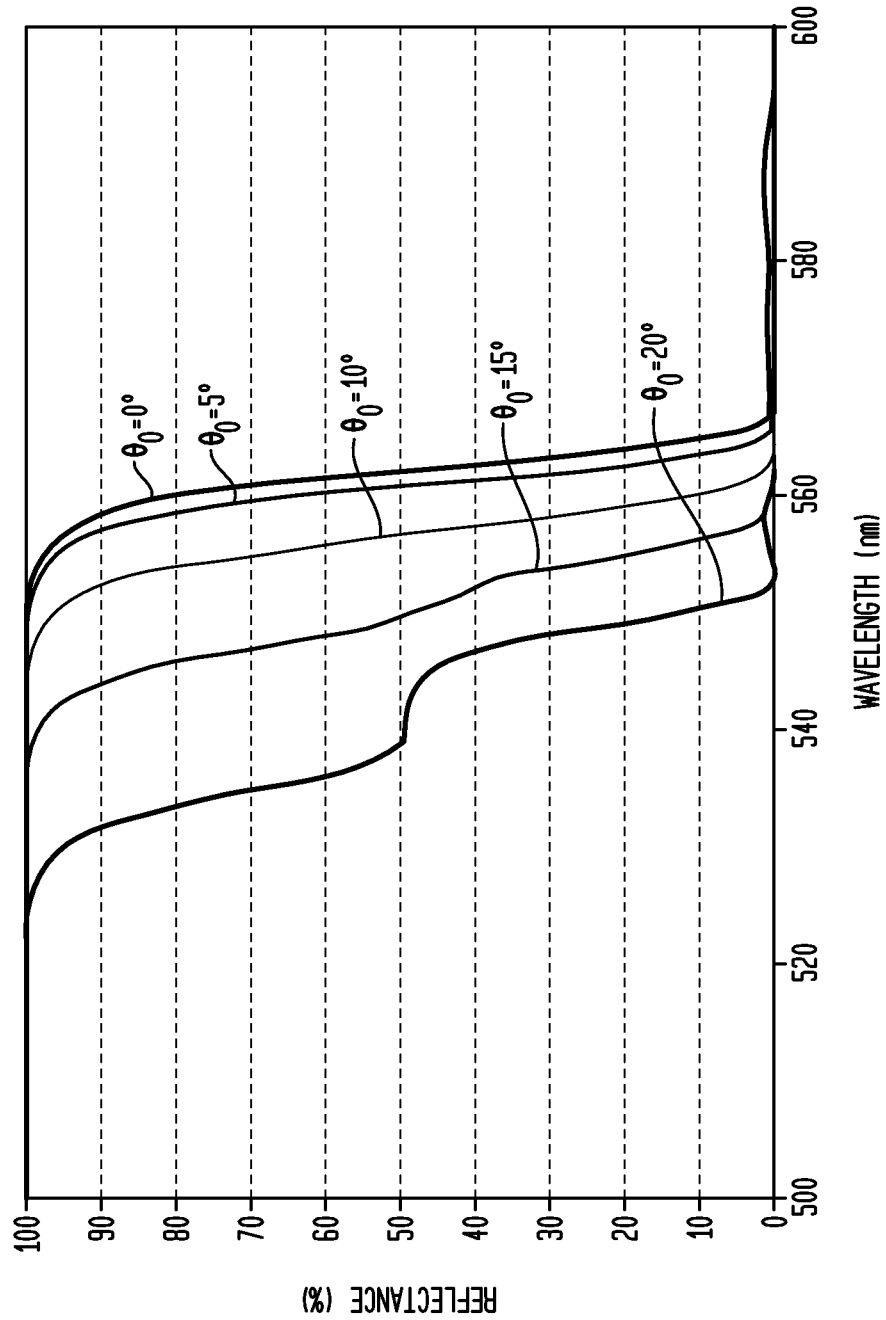
FIG. 5 is a graph of the reflectance of a nominal 560 nm coated fiber tip filter depicting the effects of the angle of incidence (AOI)
Figure 6:
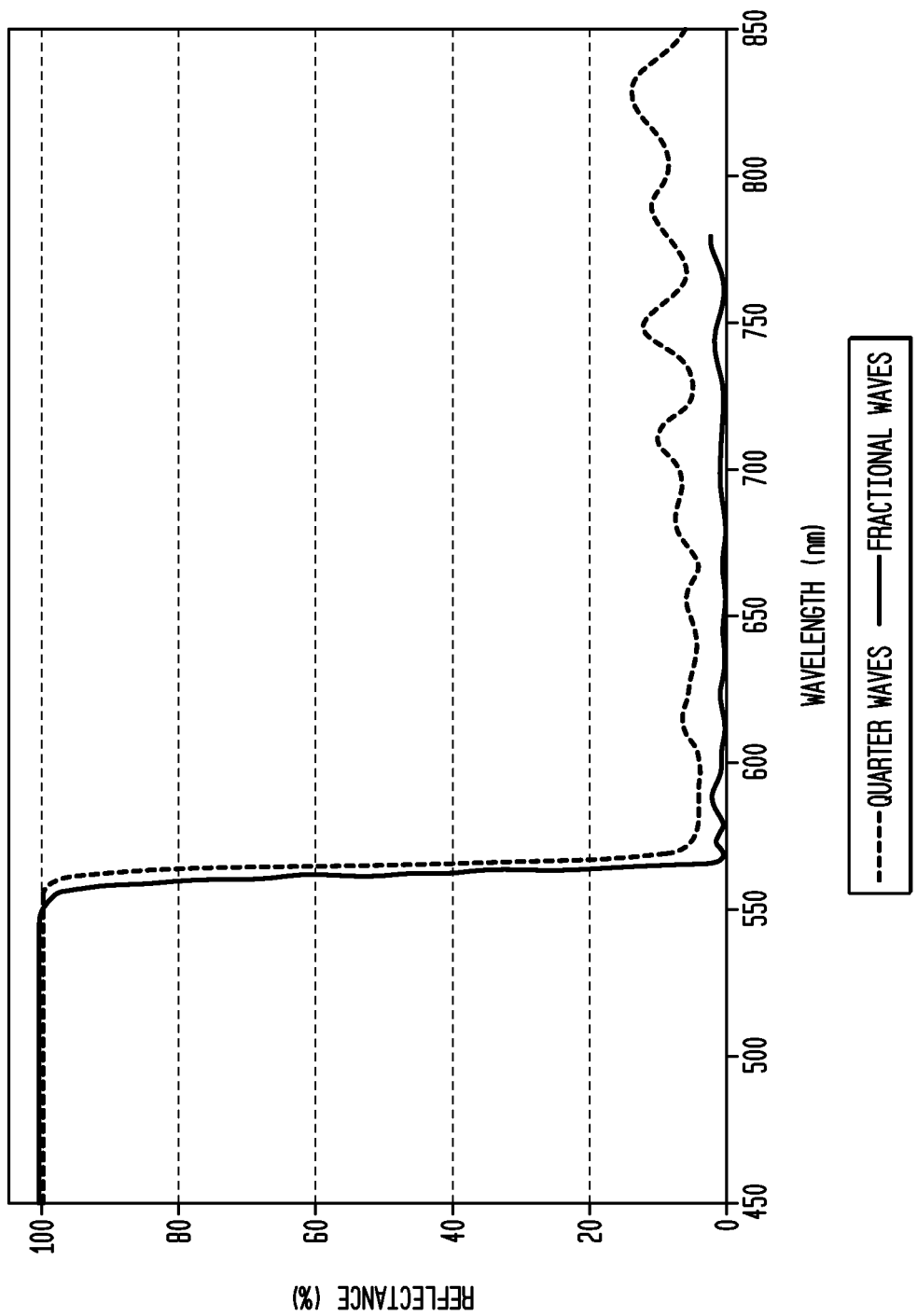
FIG. 6 is a graph of the reflectance of coated fiber tip filter with the use of quarter wave, and fractional wave thin-film layers.

Shown in FIG. 5 is the reflectance of a nominal 560 nm coated fiber tip. Experimental results indicate that coated fiber tips work well up to 10 degrees, shifting only about 2 nm towards the shorter wavelengths. It is expected that the filter performance can be further improved with Rugate designs and needles. However, it should be understood that in general there is a blue shift as the angle of incidence increases, and follows the equation:

$$2n_{eff} d \cos\theta = m\lambda \quad (2)$$

where $n_{eff}$ is the effective index of refraction of the coated fiber tip, $\theta$ is the angle of incidence at the fiber tip, and $\lambda$ is the wavelength. It should be understood that this blue shift will cause crosstalk and that the non-steep spectral edge will cause crosstalk, i.e., some wavelengths will appear in more than one bin. Our judicious choice of low angle injection minimizes this problem. Moreover, to further minimize crosstalk, non-quarter wave fractional layers may be used to eliminate the ripple in reflectance, as shown in FIG. 6.

Figure 7:
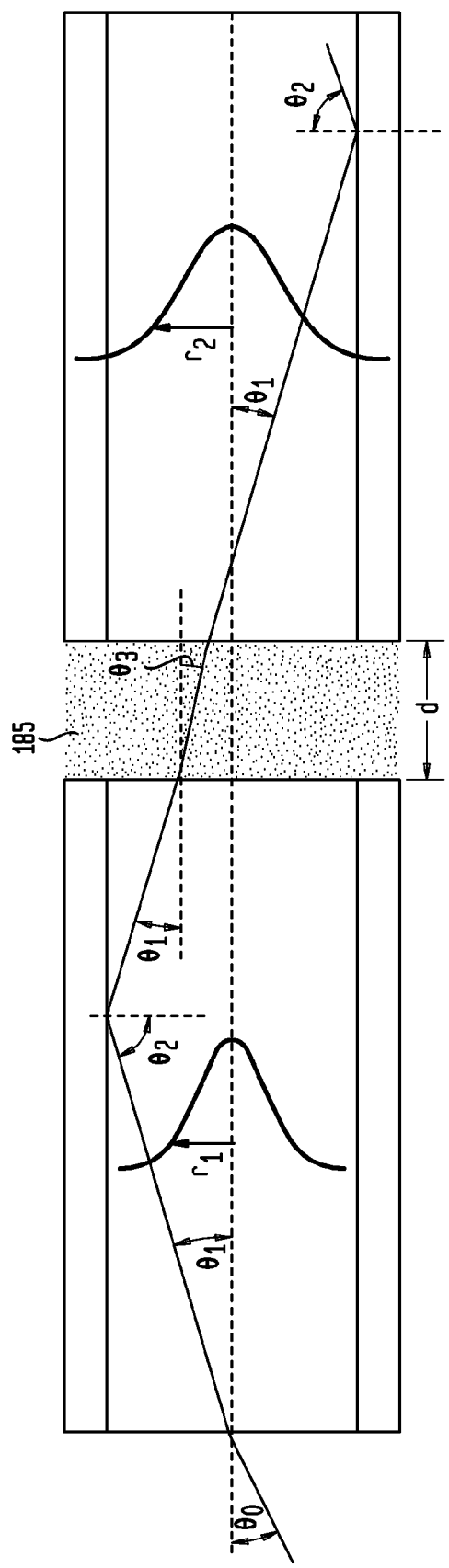
FIG. 7 is a schematic diagram depicting the path of a meridional light ray from one multi-mode fiber to another passing through a coated fiber tip filter.

To gain a better understanding of the present invention, it is noteworthy to examine the core to clad leakage during transmission through a coated fiber tip. The path of a meridional ray through the core is shown in FIG. 7. The numerical aperture (NA) of the confocal aperture is related to the slope of the ray $\theta_1$ inside the core as follows:

$$NA = \sin\theta_0 = n_{core} \sin\theta_1 \quad (3)$$

where $n_{core}$ is the index of refraction of the core of the optical fiber. Propagation from a core through a coated fiber tip to a core is subject to core to clad leakage because there no clad within the stack of interference layers. The Gaussian light wave of radius $r_1$ in the sending core spreads into a larger Gaussian light wave of radius $r_2$ as it propagates through the thin film coating. That is, the $1/e^2$ radius of the Gaussian wave expands as it passes through the coating. The tail of the expanded Gaussian light wave, however, will leak into the clad of the receiving core.

Again, applying Snell's Law for the meridional ray we have:

$$n_{core} \sin\theta_1 = n_{filter} \sin\theta_3 \quad (4)$$

The magnitude of $r_2$ can be shown to be:

$$(r_2 - r_1) = d \tan\theta_3 \quad (5)$$

where d is the thickness of the coated fiber tip, $n_{filter}$ is the effective index of refraction of the coated fiber tip, $r_1$ is the $1/e^2$ radius of the mode field diameter in the core, and $r_2$ is the radius of the expanded Gaussian light wave. The coupling efficiency can be estimated by a two dimensional integral of the expanded Gaussian light wave in a plane perpendicular to the fiber axis:

$$\int_0^{r_1} \int_0^{2\pi} \exp(-2(r/r_2)^2) r \, dr \, d\phi \quad (6)$$

where r has been integrated from zero to $r_1$ (the $1/e^2$ radius of the sending Gaussian light wave), and $\phi$ has been integrated from 0 to $2\pi$. The integral has been expressed in polar coordinates (r=radius and $\phi$=the azimuthal angle) in the plane perpendicular to the fiber axis.

Figure 8:
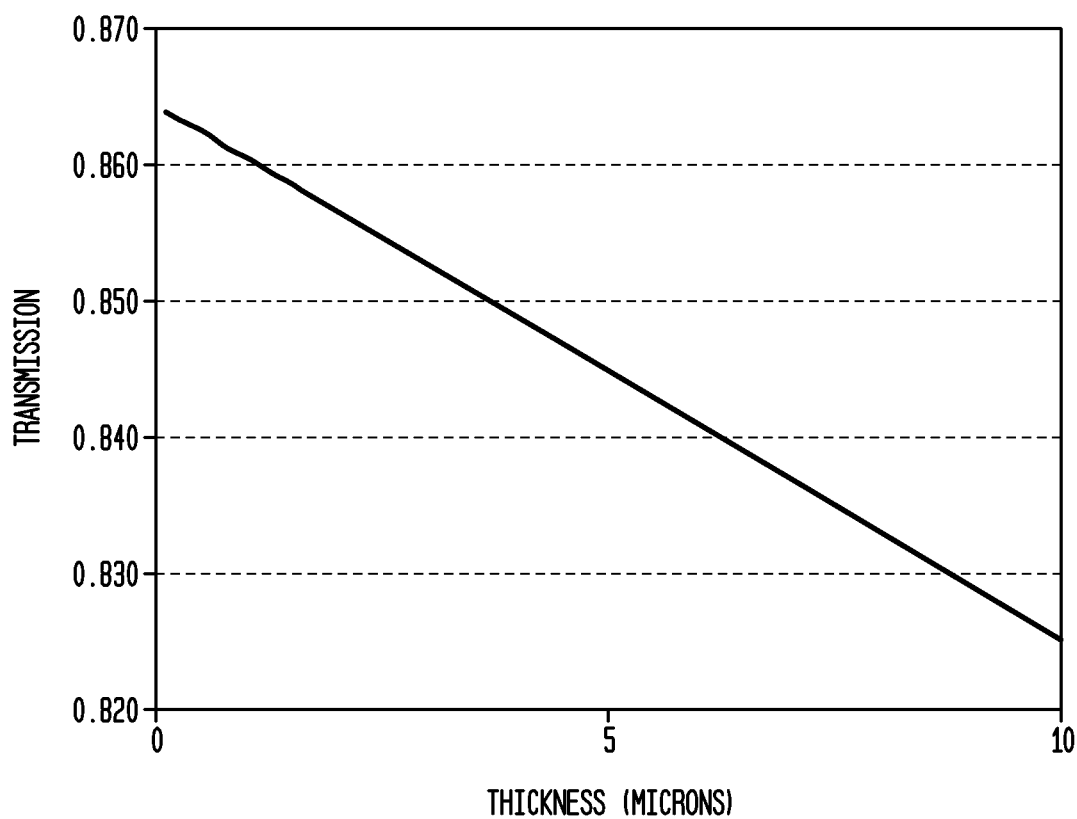
FIG. 8 is the transmission as a function of the thickness of a coated fiber tip.
Figure 9:
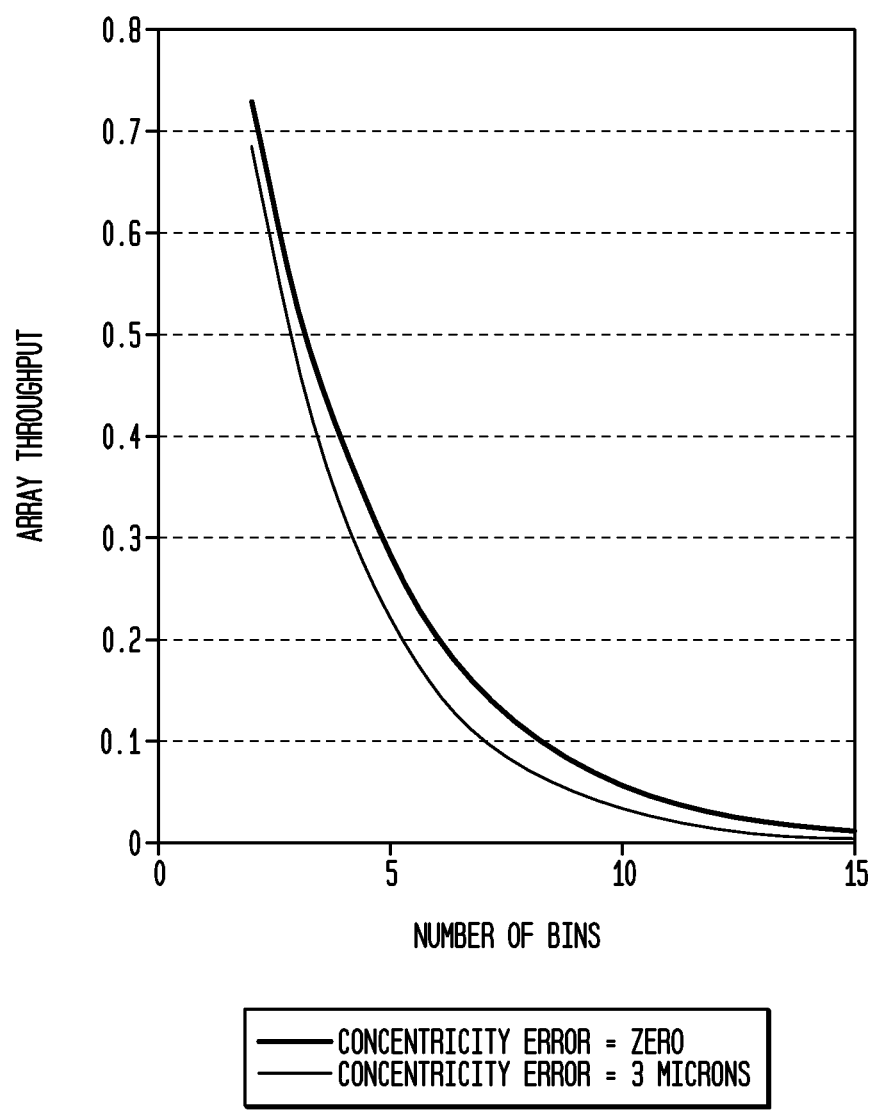
FIG. 9 is the transmission as a function of the number of bins for the system of the present invention.

Note that the loss is a function of the effective index $n_{filter}$ of coated fiber tip, and the thickness d of the coating, as well as the core-to-clad concentricity of the two mated fibers. An exemplary calculation of the 2D Gaussian integral of Eq. 8 indicates that a typical 3 μm thick fiber tip filter with an effective index of 1.89 transmits about 85% of the light into the receiving fiber core. Shown in FIG. 8 is the transmission as a function of the thickness of the thin film coating. Raising this factor (ie 0.85) to the $8^{th}$ power for a 5 bin spectral design(two passes through the first four fiber tips) indicates that 28% of the longest wavelength that enters the array of coated fiber tips will propagate back out. The above developed transmission analysis establishes that the transmission for the present invention is high enough for practical filter thicknesses. Shown in FIG. 9 is the transmission as a function of the number of bins. If the worst case concentricity is considered, the single and 5 bin designs propagate 83% and 22%, respectively, still acceptable in a practical application.

According to another embodiment, the confocal scanning system of the present invention can also be operated in a so-called "treatment mode." The fluorescence spectral images obtained can reveal the location of diseased tissue, and a subsequent scan may be used to treat the diseased tissue. Referring again to FIG. 1, on a second scan a controller 300 could be employed to increase the power level of pulsed radiation source 105 at only the locations of the diseased tissue. At sufficiently high power level, light energy from the radiation source ablates the abnormal tissue with a spatial resolution on the order of 1 to 2 microns. This spatial accuracy is much more spatially accurate than manual excision with surgical tools, and can be used to remove diseased tissue around the margins of excised tumors. Alternatively, photodynamic therapy may be used where the diseased tissue is treated with a photosensitizer and exposed selectively to the light on the second scan to photochemically destroy the diseased tissue. The wavelength of the radiation source needs to be appropriate for exciting the photosensitizer. The treatment mode laser can either be the same laser used for mapping fluorescence to detect disease, or another laser introduced into the optical system.

It should be understood that the embodiments herein above are merely illustrative of the principles of the invention. Various modifications may be made by those skilled in the art which will embody the principles of the invention and fall within the spirit and the scope thereof.

What is claimed is:

1. A system for multispectral confocal mapping of a tissue, comprising:
   an illumination source for producing an illumination beam propagating along an optical path towards the tissue;
   a first lens system for focusing said illumination beam to a focused spot on said tissue to optically induce fluorescence therefrom within a desired wavelength region;
   optically coupled to said first lens system, a confocal scanner to scan the focused spot across said tissue;
   a fiber optic spectrometer, including a plurality of multimode optical fibers operating at said desired wavelength region, one of said plurality of multimode optical fibers having an entrance aperture acting as a confocal pinhole for said confocal scanner, and said fiber optic spectrometer also including a plurality of coated fiber tips each consisting of a thin film filter deposited between the ends of two of the plurality of multimode optical fibers that are connected together to provide a temporal sequence of wavelength selective reflections of the fluorescence;
   a second lens system to focus the fluorescence from said tissue into said plurality of multimode optical fibers, said second lens system having a sufficiently low numerical aperture relative to said plurality of multimode optical fibers for the fluorescence to remain a Gaussian beam as it propagates within the plurality of multimode optical fibers; and
   a detector optically coupled to receive said temporal sequence of wavelength selective reflections to provide a suitable output indicative of the spectral components of the fluorescence.

2. The system of claim 1 wherein the wavelength selective reflections from the plurality of coated fiber tips are spectrally selected to detect a specific type of tissue disease.

3. The system of claim 1 wherein said plurality of coated fiber tips comprise a serial array of coated fiber tips.

4. The system of claim 3 further comprising a plurality of optical delay lines, with an associated optical delay line disposed between successive coated fiber tips which delays the wavelength selective reflections.

5. The system of claim 1 further comprising a controller for increasing the power level of said illumination source.

6. The system of claim 1 wherein said illumination source comprises a pulsed laser to provide optical pulses.

7. The system of claim 1 wherein said first lens systems includes an endoscopic fiber bundle.

8. The system of claim 1 wherein the fluorescence is within the visible spectrum from 500-800 nm.

9. The system of claim 1 wherein said detector includes a photomultiplier tube or a single photon detector array.

10. The system of claim 1 wherein the plurality of multimode optical fibers has a core size of 10 μm.

11. The system of claim 1 wherein the plurality of multimode optical fibers has a core size of 62.5 μm.

12. The system of claim 1 wherein said plurality of multimode optical fibers has a numerical aperture of between 0.12 and 0.4.

13. A confocal scanning system for generating multispectral images of fluorescence from a tissue, comprising:
   a laser for producing a pulsed excitation beam;
   a first lens system to focus said pulsed excitation beam to a focused spot on said tissue to induce fluorescence from the tissue within a desired wavelength region;
   a confocal scanner optically coupled to said first lens system to scan said focused spot across said tissue;
   a fiber optic spectrometer optically coupled to said confocal scanner, said fiber optic spectrometer including a plurality of multimode optical fibers operating at the desired wavelength region, first and second serial arrays of coated fiber tips each consisting of a thin film filter deposited between the ends of two of the plurality of the multimode optical fibers that are connected together so that each coated fiber tip is immersed between multimode optical fibers on both sides, each of said coated fiber tips reflecting a corresponding spectral component of the fluorescence;
   a second lens system to inject the fluorescence from the tissue at low injection angles into the plurality of multimode optical fibers such that the fluorescence remains as a Gaussian beam as it propagates within the plurality of multimode optical fibers;
   a plurality of optical delay lines, with an associated optical delay line disposed between successive coated fiber tips which delays the spectral components reflected from the coated fiber tips to space apart each of the spectral components from one another in the time domain; and
   a detector optically coupled to said fiber optic spectrometer for converting said spectral components of the fluorescence into a corresponding electrical signal.

14. The system of claim 13 wherein the coated fiber tips reflect corresponding spectral components of the fluorescence to detect a specific type of tissue disease.

15. The system of claim 13 further comprising a controller to increase the power level of said pulsed excitation beam to treat diseased tissue in locations revealed by fluorescent maps.

16. The system of claim 13 wherein said first lens system includes an endoscope fiber bundle.

17. The system of claim 13 wherein the entrance aperture of one of the plurality of multimode fibers acts as a confocal pinhole.

18. The system of claim 13 wherein said detector includes a photomultiplier tube or a single photon detector array.

19. The system of claim 13 wherein said plurality of multimode optical fibers has a numerical aperture of between 0.12 and 0.4.

* * * * *